United States Patent
Penzo et al.

(10) Patent No.: US 12,103,988 B2
(45) Date of Patent: Oct. 1, 2024

(54) GAS-PHASE PROCESS FOR PREPARING ETHYLENE POLYMERS (71) Applicant: Basell Polyolefine GmbH, Wesseling (DE)

(72) Inventors: Giuseppe Penzo, Ferrara (IT); Gerhardus Meier, Houston, TX (US); Ulf Schueller, Weiterstadt (DE); Pietro Baita, Ferrara (IT); Giulia Mei, Ferrara (IT); Elke Damm, Bad Vilbel (DE)

(73) Assignee: Basell Polyolefine GmbH, Wesseling (DE)

( * ) Notice: Subject to any disclaimer, the term of this patent is extended or adjusted under 35 U.S.C. 154(b) by 645 days.

(21) Appl. No.: 17/312,822

(22) PCT Filed: Dec. 16, 2019

(86) PCT No.: PCT/EP2019/085422
§ 371 (c)(1),
(2) Date: Jun. 10, 2021

(87) PCT Pub. No.: WO2020/127098
PCT Pub. Date: Jun. 25, 2020

(65) Prior Publication Data
US 2021/0332167 A1    Oct. 28, 2021

(30) Foreign Application Priority Data

Dec. 18, 2018  (EP) .................................. 18213407

(51) Int. Cl.
C08F 210/16    (2006.01)
B01J 8/00    (2006.01)
(Continued)

(52) U.S. Cl.
CPC ........... *C08F 110/02* (2013.01); *B01J 8/0055* (2013.01); *B01J 8/1827* (2013.01); *B01J 8/1863* (2013.01);
(Continued)

(58) Field of Classification Search
CPC ............. C08F 2/34; C08F 2/01; C08F 210/16
See application file for complete search history.

(56) References Cited

U.S. PATENT DOCUMENTS 4,399,054 A    8/1983   Ferraris et al.
5,733,987 A    3/1998   Covezzi et al.
(Continued)

FOREIGN PATENT DOCUMENTS

EP    192427 A1    8/1986
EP    2602269 A1 *    6/2013 .............. C08F 10/00
(Continued)

OTHER PUBLICATIONS

The International Search Report and Written Opinion for PCT/EP2019/085422 mailed Apr. 7, 2020.
(Continued)

Primary Examiner — Rip A Lee (57) ABSTRACT

A process for preparation of an ethylene polymer in a gas-phase polymerization unit comprising a gas-phase polymerization reactor by homopolymerizing ethylene or copolymerizing ethylene and one or more $C_4$-$C_{12}$-1-alkenes in a reaction gas made from or containing propane as polymerization diluent in the presence of a pre-activated polymerization catalyst, wherein a purified propane feed stream made from or containing at least 99 mol % propane and from 0.1 to 100 ppm mol propylene is fed to the gas-phase polymerization unit.

20 Claims, 2 Drawing Sheets (51) Int. Cl.

| | | |
|---|---|---|
| *B01J 8/18* | (2006.01) | |
| *B01J 8/26* | (2006.01) | |
| *B01J 21/04* | (2006.01) | |
| *B01J 23/42* | (2006.01) | |
| *B01J 23/44* | (2006.01) | |
| *B01J 23/72* | (2006.01) | |
| *C08F 2/01* | (2006.01) | |
| *C08F 2/34* | (2006.01) | |
| *C08F 110/02* | (2006.01) | |

(52) U.S. Cl.
CPC .............. *B01J 8/1881* (2013.01); *B01J 8/26* (2013.01); *B01J 21/04* (2013.01); *B01J 23/42* (2013.01); *B01J 23/44* (2013.01); *B01J 23/72* (2013.01); *C08F 210/16* (2013.01); *C08F 2/01* (2013.01); *C08F 2/34* (2013.01)

(56) References Cited

U.S. PATENT DOCUMENTS

| | | | |
|---|---|---|---|
| 6,413,477 B1 | 7/2002 | Govoni et al. | |
| 6,927,260 B2 * | 8/2005 | Berhalter | B01J 8/1809 |
| | | | 526/90 |
| 7,582,723 B2 * | 9/2009 | Penzo | B01J 8/006 |
| | | | 528/483 |
| 8,198,383 B2 | 6/2012 | Mazzucco et al. | |
| 9,458,259 B2 * | 10/2016 | Penzo | C08F 10/02 |
| 2016/0108147 A1 | 4/2016 | Penzo et al. | |

FOREIGN PATENT DOCUMENTS

| | | |
|---|---|---|
| EP | 2803680 A1 | 11/2014 |
| JP | 2013129606 A | 7/2013 |
| JP | 2017078171 A | 4/2017 |
| RU | 2475501 C2 | 2/2013 |
| WO | 9704015 A1 | 2/1997 |
| WO | 0002929 A1 | 1/2000 |
| WO | 03/014169 A2 | 2/2003 |
| WO | 2006082007 A1 | 8/2006 |
| WO | 2008022900 A1 | 2/2008 |
| WO | 2008058839 A2 | 5/2008 |
| WO | 2013083548 A2 | 6/2013 |
| WO | 2014090860 A1 | 6/2014 |
| WO | 2016121622 A1 | 8/2016 |
| WO | 2018022199 A1 | 2/2018 |
| WO | 2018087214 A1 | 5/2018 |

OTHER PUBLICATIONS

GHC Standard Specification, Spec 2716 Propane (4.0), Revision: 7 Verantwortlich: Produktmanager—Freigabe: Murat Metin Sep. 20, 2018.

* cited by examiner

GAS-PHASE PROCESS FOR PREPARING ETHYLENE POLYMERS

This application is the U.S. National Phase of PCT International Application PCT/EP2019/085422, filed Dec. 16, 2019, claiming benefit of priority to European Patent Application No. 18213407.2, filed Dec. 18, 2018, the disclosures of which are incorporated herein by reference in their entirety.

FIELD OF THE INVENTION

In general, the present disclosure relates to the field of chemistry. More specifically, the present disclosure relates to polymer chemistry. In particular, the present disclosure relates to processes for the preparation of an ethylene polymer in a gas-phase polymerization reactor.

BACKGROUND OF THE INVENTION

Gas-phase polymerization processes are processes for the polymerization of ethylene, such as homopolymerizing ethylene or copolymerizing ethylene with other olefins. In some instances, reactors for carrying out these gas-phase polymerizations are fluidized-bed reactors, stirred gas-phase reactors or multizone circulating reactors with two distinct interconnected gas-phase polymerization zones. In some instances, these processes are carried out in a gas phase made from or containing ethylene and comonomers. In some instances, other gaseous components are present. In some instances, the other gaseous components are polymerization diluents or hydrogen. In some instances, the polymerization diluents are nitrogen or alkanes. In some instances, hydrogen is used as a molecular weight modifier for low-molecular weight reaction products. In some instances, the products are solid polyethylene particles which are formed by polymerization catalyst systems. In some instances, the polymerization catalyst systems are made from or containing a solid catalyst component.

Inert components of the reaction gas, wherein the polymerization is carried out, act as polymerization diluent and allow control of the polymerization rate. In some instances, the reaction gas is made from or containing propane. In some instances, the discharged polyethylene is degassed. In some instances, the reaction gas, which is separated from the discharged polyethylene particles, is collected, recompressed to the polymerization pressure, and recycled to the gas-phase polymerization reactors. In some instances, losses of reaction gas are lost. In those instances, these lost amounts are replaced by a fresh feed.

In gas-phase polymerization processes, which are carried out in the presence of a reaction gas made from or containing propane as polymerization diluent, propane may also be used for additional purposes. In some instances and for preventing carry-over of reaction gas of a first polymerization stage from the fluidized-bed reactor to a second gas-phase polymerization reactor in the transfer of the polyolefin particles, propane is introduced into the discharge pipe in an amount that an upward stream of the propane is induced in the bed of polyolefin particles above the propane introduction point and the polyolefin particles are withdrawn from the lower end of the discharge pipe. A further use of propane in gas-phase polymerization processes is the utilization of propane as liquid phase in a catalyst pre-activating step, wherein a solid catalyst component is contacted with cocatalysts, such as aluminum alkyl compounds, and optionally further electron donor compounds before being introduced into a polymerization step.

Organometallic compounds like aluminum alkyls, which can be employed as cocatalysts for the polymerization reaction, can be used as scavengers of polar compounds brought into the polymerization reactor and act as catalyst poisons. The reaction of the organometallic compounds with polar compounds changes the availability of the organometallic compounds as cocatalyst for the ethylene polymerization, resulting in altered reactor yields and product properties. Even more demanding is the situation where two or more polymerization reactors are operated in series, where active catalyst within the ethylene polymer particles flows from one reactor to a subsequent reactor, and various feed streams are fed to each reactor. Variations in the amounts of available organometallic compound in the individual polymerization reactors may result in changes in the properties of the final ethylene polymers; however, fluctuations in the impurity levels of the feed streams might complicate adjustments.

There are various processes for purifying monomer feed streams. In some instances, a process has a hydrogenation stage, wherein the "feed ethylene" is reacted with hydrogen to remove the acetylene by catalytic hydrogenation to form ethylene and part of the ethylene is converted into ethane, and a polymerization stage, wherein the ethylene leaving the hydrogenation stage is reacted in the gas phase to form polyethylene, and the fluidizing gas used in the fluidized-bed reactor is made from or containing, on entering the reactor, ethylene and from 20 to 70% by volume of ethane, based on the total volume of the fluidizing gas. In some instances, a process for purifying ethylene produced from a methanol-to-olefins facility includes the steps of (a) passing an olefin stream comprising at least 99 mol % ethylene through a sulfur guard bed to remove sulfur compounds, (b) contacting the effluent from (a) with a hydrogenation catalyst, (c) passing the effluent from (b) through a copper-metal containing catalyst bed to remove carbon monoxide and hydrogen and (d) passing the effluent from (c) through a desiccant to remove polar contaminants and yield a purified ethylene stream comprising greater than or equal to 99.875 mol % ethylene.

In some instances, impurities are brought into the polymerization process by other streams such as the propane feed stream. Utilizing a propane of a low purity for replacing the propane losses in the polymerization process could result in a consumption of organometallic compounds used as cocatalysts due to a reaction with polar impurities, thereby resulting in fluctuating concentrations of the organometallic compounds in the polymerization reactors and influencing negativity the reactor yields and selectivities. Utilizing a propane of a low purity for replacing the propane losses could also affect the catalyst properties by side reactions of catalyst components with polar impurities in the polymerization reactor(s), including in the pre-activation step. Introducing nonpolar impurities like alkenes with the propane feed stream into the polymerization reactor could negatively impact the polymerization process. Lower molecular weight alkenes such as propylene could be incorporated as comonomers in the polyethylene chains, thereby affecting adversely the polymer properties. A gas composition used for inertization purposes and containing polymerizable components could cause operational problems by sheeting or lump formation. The presence of lower molecular weight alkenes such as propylene in the pre-activation step could lead to the formation of high molecular weight polymers due to an uncontrolled polymerization of the alkenes with the activated catalyst in the absence of hydrogen. Such high molecular weight polymers are however not miscible with ethylene polymers and could reduce the quality of the produced polyethylenes, for example by formation of gels.

SUMMARY OF THE INVENTION

In a general embodiment, the present disclosure provides a process for the preparation of an ethylene polymer, including the step of forming an ethylene polymer in particle form in a gas-phase polymerization unit having a gas-phase polymerization reactor by homopolymerizing ethylene or copolymerizing ethylene and one or more $C_4$-$C_{12}$-1-alkenes at temperatures from 20 to 200° C. and pressures of from 0.5 to 10 MPa in a reaction gas made from or containing propane as polymerization diluent in the presence of a pre-activated polymerization catalyst, wherein a purified propane feed stream made from or containing at least 99% mol propane and not more than 100 ppm-mol propylene is fed to the gas-phase polymerization unit and the purification has been carried out by passing a hydrocarbon stream through hydrocarbon purification units which reduce at least the concentration of propylene, acetylene, carbon monoxide, carbon dioxide, oxygen and water contained in the hydrocarbon stream.

In some embodiments, the purified propane feed stream fed to the gas-phase polymerization unit is made from or containing not more than 0.03 ppm-mol carbon monoxide, not more than 0.4 ppm-mol carbon dioxide, not more than 2.0 ppm-mol oxygen, not more than 3.0 ppm-mol acetylene, and not more than 2.0 ppm-mol water.

In some embodiments, the pre-activation of the polymerization catalyst is carried out by contacting, in liquid propane as diluent, a solid catalyst component with an organometallic compound and optionally an electron donor compound to form a pre-activated polymerization catalyst.

In some embodiments, the propane used as liquid diluent for the pre-activation of the polymerization catalyst is taken from the purified propane feed stream.

In some embodiments, a hydrocarbon purification unit for preparing the purified propane stream is a catalytic hydrogenation unit.

In some embodiments, the catalytic hydrogenation unit is made from or containing a hydrogenation catalyst which is a platinum- or palladium-based composition on an alumina support.

In some embodiments, a part of the hydrocarbon stream having passed the catalytic hydrogenation unit is recycled to a position upstream of the catalytic hydrogenation unit and mixed with the hydrocarbon stream to be hydrogenated.

In some embodiments, the purification of the propane feed stream occurs by subsequently passing a hydrocarbon stream through first a purification unit made from or containing a Cu based catalyst, then passing the resulting stream through a catalytic hydrogenation unit, thereafter passing the resulting stream through a separation unit and afterwards passing the resulting stream through a drying unit.

In some embodiments, the hydrocarbon stream for preparing the purified propane feed stream is a purified propylene stream made from or containing at least 99 mol % propylene.

In some embodiments, the ethylene polymer is a multimodal ethylene polymer and the gas-phase polymerization unit has a reactor cascade of two or more gas-phase polymerization reactors which has a first polymerization reactor, into which the pre-activated polymerization catalyst is fed, and one or more subsequent polymerization reactors, which receive the polymerization catalyst in active form incorporated in ethylene polymer particles formed in the preceding reactors.

In some embodiments, the first reactor of the reactor cascade is a fluidized-bed reactor.

In some embodiments, the fluidized-bed reactor has a polymer discharge pipe, which contains a bed of ethylene polymer particles which moves from top to bottom of the discharge pipe, wherein propane is introduced into the discharge pipe in an amount that an upward stream of the propane is induced in the bed of ethylene polymer particles above the propane introduction point.

In some embodiments, a subsequent polymerization reactor is a multizone circulating reactor wherein a first polymerization zone is a riser, wherein growing polyolefin particles flow upwards under fast fluidization or transport conditions, and a second polymerization zone is a downcomer, wherein the growing polyolefin particles flow downward in a densified form, wherein the riser and the downcomer are interconnected and polyolefin particles leaving the riser enter the downcomer and polyolefin particles leaving the downcomer enter the riser, thereby establishing a circulation of polyolefin particles through the riser and the downcomer.

In some embodiments, the ethylene polymer is a high density polyethylene having a density determined according to DIN EN ISO 1183-1:2004 at 23° C. from 0.935 g/cm³ to 0.970 g/cm³.

DETAILED DESCRIPTION OF THE INVENTION

In some embodiments, the present disclosure provides a process for preparing an ethylene polymer including the step of homopolymerizing ethylene or copolymerizing ethylene with one or more other olefins as comonomer(s) in the presence of a polymerization catalyst. In some embodiments, the olefins employed in the process are ethylene, alternatively 1-olefins, that is, hydrocarbons having terminal double bonds, without being restricted thereto. In some embodiments, the olefins are nonpolar olefinic compounds. In some embodiments, the 1-olefins are selected from the group consisting of linear or branched $C_4$-$C_{12}$-1-alkenes and conjugated and nonconjugated dienes. In some embodiments, the linear $C_4$-$C_{12}$-1-alkenes are linear $C_4$-$C_{10}$-1-alkenes. In some embodiments, the linear $C_4$-$C_{10}$-1-alkenes are selected from the group consisting of 1-butene, 1-pentene, 1-hexene, 1-heptene, 1-octene, and 1-decene. In some embodiment, the branched $C_4$-$C_{12}$-1-alkenes are branched $C_2$-$C_{10}$-1-alkenes. In some embodiments, the branched $C_2$-$C_{10}$-1-alkene is 4-methyl–1-pentene. In some embodiments, the conjugated and nonconjugated dienes are selected from the group consisting of 1,3-butadiene, 1,4-hexadiene, and 1,7-octadiene. In some embodiments, the olefins have the double bond as part of a cyclic structure, with one or more ring systems. In some embodiments, the olefins are selected from the group consisting of cyclopentene, norbornene, tetracyclododecene, methylnorbornene, and dienes. In some embodiments, the dienes are selected from the group consisting of 5-ethylidene-2-norbornene, norbornadiene, and ethylnorbornadiene. In some embodiments, the ethylene is copolymerized with mixtures of two or more olefins. In some embodiments, the comonomers in the ethylene polymerization are used in an amount of up to 20 wt. %, alternatively from 0.01 wt. % to 15 wt. %, alternatively from 0.05 wt. % to 12 wt. %. In some embodiments, the comonomers are made from or containing $C_4$-$C_8$-1-alkenes. In some embodiments, the $C_4$-$C_8$-1-alkenes are selected from the group consisting of 1-butene, 1-pentene, 1-hexene and 1-octene. In some embodiments, the ethylene is copolymerized with from 0.1 wt. % to 12 wt. % of 1-hexene and/or 1-butene, alternatively with from 0.1 wt. % to 12 wt. % of 1-hexene.

Gas-phase polymerization processes are processes wherein solid polymers are obtained from a gas-phase made from or containing the monomer or the monomers. Such processes are carried out by feeding a solid pre-activated polymerization catalyst into a gas-phase polymerization reactor and polymer grows on these particles. The resulting polyethylene particles have varying morphology and size, which depend on the catalyst morphology and size and on polymerization conditions. In some embodiments, the mean particle diameter of the polyethylene particles is in the range of from about 500 to about 3000 μm.

In some embodiments, the homopolymerization or copolymerization of ethylene is carried out using Phillips catalysts based on chromium oxide, Ziegler- or Ziegler-Natta-catalysts, or single-site catalysts. As used herein, the term "single-site catalysts" refers to catalysts based on chemically uniform transition metal coordination compounds. In some embodiments, mixtures of two or more of these catalysts are used for the polymerization of olefins. As used herein, the mixed catalysts are designated "hybrid catalysts."

In some embodiments, the catalysts are of the Ziegler type. In some embodiments, the Ziegler-type catalysts are made from or containing a compound of titanium or vanadium, a compound of magnesium and optionally an electron donor compound and/or a particulate inorganic oxide as a support material. In some embodiments, the gas-phase alpha-olefin polymerization process is carried out in the presence of a Ziegler type catalyst made from or containing the reaction product of an aluminum alkyl with a titanium compound supported on a magnesium halide.

In some embodiments, the titanium compounds are halides or alkoxides of trivalent or tetravalent titanium. In some embodiments, the titanium compounds are titanium alkoxy halogen compounds or mixtures of various titanium compounds. In some embodiments, the titanium compounds are selected from the group consisting of $TiBr_3$, $TiBr_4$, $TiCl_3$, $TiCl_4$, $Ti(OCH_3)Cl_3$, $Ti(OC_2H_5)Cl_3$, $Ti(O-i-C_3H_7)Cl_3$, $Ti(O-n-C_4H_9)Cl_3$, $Ti(OC_2H_5)Br_3$, $Ti(O-n-C_4H_9)Br_3$, $Ti(OCH_3)_2Cl_2$, $Ti(OC_2H_5)_2Cl_2$, $Ti(O-n-C_4H_9)_2Cl_2$, $Ti(OC_2H_5)_2Br_2$, $Ti(OCH_3)_3Cl$, $Ti(OC_2H_5)_3Cl$, $Ti(O-n-C_4H_9)_3Cl$, $Ti(OC_2H_5)_3Br$, $Ti(OCH_3)_4$, $Ti(OC_2H_5)_4$ and $Ti(O-n-C_4H_9)_4$. In some embodiments, the titanium compounds are made from or containing chlorine as the halogen. In some embodiments, the titanium compounds are titanium halides consist of halogen and titanium. In some embodiments, the titanium compounds are titanium chlorides, alternatively titanium tetrachloride. In some embodiments, the vanadium compounds are selected from the group consisting of vanadium halides, vanadium oxyhalides, vanadium alkoxides, and vanadium acetylacetonates. In some embodiments, the vanadium compounds have oxidation states 3 to 5.

In some embodiments, the production of the solid component uses a compound of magnesium. In some embodiments, the magnesium compounds are made from or containing a halogen and magnesium. In some embodiments, the magnesium compounds are magnesium halides. In some embodiments, the halide is selected from the group consisting of chloride and bromide. In some embodiments, the magnesium halides are obtained by reaction with halogenating agents. In some embodiments, the halogens are chlorine, bromine, iodine or fluorine or mixtures of two or more halogens, alternatively chlorine or bromine, alternatively chlorine.

In some embodiments, the magnesium compounds are magnesium chlorides or magnesium bromides. In some embodiments, the magnesium halides are obtained from magnesium alkyls, magnesium aryls, magnesium alkoxy compounds or magnesium aryloxy compounds or Grignard compounds. In some embodiments, the halogenating agents are halogens, hydrogen halides, $SiCl_4$ or $CCl_4$, alternatively chlorine or hydrogen chloride.

In some embodiments, the magnesium compounds are halogen-free. In some embodiments, the halogen-free compounds of magnesium are selected from the group consisting of diethylmagnesium, di-n-propylmagnesium, diisopropylmagnesium, di-n-butylmagnesium, di-sec-butylmagnesium, di-tert-butylmagnesium, diamylmagnesium, n-butylethylmagnesium, n-butyl-sec-butylmagnesium, n-butyloctylmagnesium, diphenylmagnesium, diethoxymagnesium, di-n-propyloxymagnesium, diisopropyloxymagnesium, di-n-butyloxymagnesium, di-sec-butyloxymagnesium, di-tert-butyloxymagnesium, diamyloxymagnesium, n-butyloxyethoxymagnesium, n-butyloxy-sec-butyloxymagnesium, n-butyloxyoctyloxymagnesium and diphenoxymagnesium. In some embodiments, the halogen-free compounds of magnesium are selected from the group consisting of n-butylethylmagnesium and n-butyloctylmagnesium.

In some embodiments, the Grignard compounds are selected from the group consisting of methylmagnesium chloride, ethylmagnesium chloride, ethylmagnesium bromide, ethylmagnesium iodide, n-propylmagnesium chloride, n-propylmagnesium bromide, n-butylmagnesium chloride, n-butylmagnesium bromide, sec-butylmagnesium chloride, sec-butylmagnesium bromide, tert-butylmagnesium chloride, tert-butylmagnesium bromide, hexylmagnesium chloride, octylmagnesium chloride, amylmagnesium chloride, isoamylmagnesium chloride, phenylmagnesium chloride and phenylmagnesium bromide.

In some embodiments, the magnesium compounds for producing the solid catalyst components are di($C_1$-$C_{10}$-alkyl)magnesium compounds. In some embodiments, the Ziegler- or Ziegler-Natta-catalyst is made from or containing a transition metal selected from the group consisting of titanium, zirconium, vanadium, and chromium.

In some embodiments, electron donor compounds for preparing Ziegler type catalysts are selected from the group consisting of alcohols, glycols, esters, ketones, amines, amides, nitriles, alkoxysilanes and aliphatic ethers. In some embodiments, these electron donor compounds are used alone, in mixtures with each other, or with additional electron donor compounds.

In some embodiments, the alcohols have the formula $R^1OH$, wherein the $R^1$ group is a $C_1$-$C_{20}$ hydrocarbon group. In some embodiments, $R^1$ is a $C_1$-$C_{10}$ alkyl group. In some embodiments, the alcohols are selected from the group consisting of methanol, ethanol, iso-propanol and n-butanol. In some embodiments, glycols have a total number of carbon atoms lower than 50. In some embodiments, the glycols are the 1,2 or 1,3 glycols having a total number of carbon atoms lower than 25. In some embodiments, the glycols are selected from the group consisting of ethylene glycol, 1,2-propylene glycol and 1,3-propylene glycol. In some embodiments, the esters are the alkyl esters of $C_1$-$C_{20}$ aliphatic carboxylic acids, alternatively $C_1$-$C_8$ alkyl esters of aliphatic mono carboxylic acids. In some embodiments, the $C_1$-$C_8$ alkyl esters of aliphatic mono carboxylic acids are selected from the group consisting of ethyl acetate, methyl formate, ethyl formate, methyl acetate, propyl acetate, i-propyl acetate, n-butyl acetate, and i-butyl acetate. In some embodiments, the amines have the formula $NR^2_3$, wherein the $R^2$ groups are, independently, hydrogen or a $C_1$-$C_{20}$ hydrocarbon group with the proviso that the $R^2$ groups are not simultaneously hydrogen. In some embodiments, $R^2$ is a $C_1$-$C_{10}$ alkyl group. In some embodiments, the amines are selected from the group consisting of diethylamine, diisopropylamine and triethylamine. In some embodiments, the amides have the formula $R^3CONR^4_2$, wherein $R^3$ and $R^4$ are, independently, hydrogen or a $C_1$-$C_{20}$ hydrocarbon group. In some embodiments, the amides are selected from the group consisting of formamide and acetamide. In some embodiments, the nitriles have the formula $R^1CN$, wherein $R^1$ has the same meaning given above. In some embodiments, the nitrile is acetonitrile. In some embodiments, the alkoxysilanes have the formula $R^5_aR^6_bSi(OR^7)_c$, wherein a and b are integers from 0 to 2, c is an integer from 1 to 4 and the sum (a+b+c) is 4; and $R^5$, $R^6$, and $R^7$, are alkyl, cycloalkyl or aryl radicals with 1-18 carbon atoms optionally containing heteroatoms. In some embodiments, the alkoxysilanes are the silicon compounds, wherein a is 0 or 1, c is 2 or 3, $R^6$ is an alkyl or cycloalkyl group, optionally containing heteroatoms, and $R^7$ is methyl. In some embodiments, the alkoxysilanes are selected from the group consisting of methyltrimethoxysilane, dimethyldimethoxysilane, trimethylmethoxysilane and t-butyltrimethoxysilane.

In some embodiments, the electron donor compounds are selected from the group consisting of amides, esters, and alkoxysilanes.

In some embodiments, catalysts of the Ziegler type are polymerized in the presence of an organometallic compound as cocatalyst. In some embodiments, the cocatalysts are organometallic compounds of metals of Groups 1, 2, 12, 13 or 14 of the Periodic Table of Elements, alternatively organometallic compounds of metals of group 13, alternatively organoaluminum compounds. In some embodiments, the cocatalysts are selected from the group consisting of organometallic alkyls, organometallic alkoxides, and organometallic halides.

In some embodiments, the organometallic compounds are selected from the group consisting of lithium alkyls, magnesium alkyls, zinc alkyls, magnesium alkyl halides, aluminum alkyls, silicon alkyls, silicon alkoxides and silicon alkyl halides. In some embodiments, the organometallic compounds are selected from the group consisting of aluminum alkyls and magnesium alkyls. In some embodiments, the organometallic compounds are aluminum alkyls, alternatively trialkylaluminum compounds or compounds wherein an alkyl group is replaced by a halogen atom. In some embodiments, the halogen atom is chlorine or bromine. In some embodiments, the aluminum alkyls are trimethylaluminum, triethylaluminum, tri-isobutylaluminum, tri-n-hexylaluminum, diethylaluminum chloride, or mixtures thereof.

In some embodiments, the process for the preparation of ethylene polymers is carried out in the presence of a pre-activated polymerization catalyst. In some embodiments, the pre-activation of the polymerization catalyst is carried out by contacting, in liquid propane as diluent, a solid catalyst component with an organometallic compound and optionally an electron donor compound to form a pre-activated polymerization catalyst. In some embodiments, the catalyst pre-activation is carried out in a single pre-activation vessel or in a sequence of two or more catalyst pre-activation vessels, wherein the contacting of the catalyst components occurs. In some of the embodiments, the step of contacting occurs at a temperature from −20° C. to 60° C., alternatively from 20° C. to 50° C. In some embodiments, the solid catalyst component is introduced continuously into the catalyst pre-activation vessel or into the first of sequence of catalyst pre-activation vessels.

In some embodiments, the process is carried out in a gas-phase polymerization unit having at least one gas-phase polymerization reactor. In some embodiments, the gas-phase polymerization reactors are stirred gas-phase reactors, multizone gas-phase reactors, or gas-phase fluidized-bed reactors. In some embodiments, the gas-phase reactors are horizontally or vertically stirred. In some embodiments, the gas-phase polymerization unit has a reactor cascade of two or more gas-phase polymerization reactors. In some embodiments, the gas-phase polymerization unit has equipment for feeding, pre-activating and/or pre-polymerizing a polymerization catalyst. In some embodiments, the gas-phase polymerization unit has equipment for treating the ethylene polymer particles discharged from a polymerization reactor and/or equipment for recovering components of the reaction gas concomitantly discharged with the ethylene polymer particles from a polymerization reactor.

In some embodiments, the reactors are fluidized-bed reactors, that is, reactors having a bed of polymerizing polyolefin particles which are kept in fluidized state by introducing a gas from below. In some embodiments, this gas is then taken off at the upper end of the reactor, cooled to remove the heat of polymerization and recirculated back into the reactor at the reactor's lower end.

In some embodiments, the reactors are multizone circulating reactors are as described in Patent Cooperation Treaty Publication Nos. WO 97/04015 and WO 00/02929 and have two interconnected polymerization zones, a riser, wherein the growing polyolefin particles flow upward under fast fluidization or transport conditions and a downcomer, wherein the growing polyolefin particles flow in a densified form under the action of gravity. The polyolefin particles leaving the riser enter the downcomer and the polyolefin particles leaving the downcomer are reintroduced into the riser, thereby establishing a circulation of polymer between the two polymerization zones and the polymer is passed alternately a plurality of times through these two zones. In some embodiments, the two polymerization zones of a multizone circulating reactor operate with different polymerization conditions by establishing different polymerization conditions in the riser and the downcomer. For this purpose and in some embodiments, the gas mixture leaving the riser and entraining the polyolefin particles is partially or totally prevented from entering the downcomer. In some embodiments, the particles are prevented entry by feeding a barrier fluid in form of a gas and/or a liquid mixture into the downcomer. In some embodiments, the gas/liquid mixture is fed in the upper part of the downcomer. In some embodiments, the barrier fluid has a composition different from that of the gas mixture present in the riser. In some embodiments, the amount of added barrier fluid is adjusted such that an upward flow of gas countercurrent to the flow of the polyolefin particles is generated, acting as a barrier to the gas mixture entrained among the particles coming from the riser. In some embodiments, the countercurrent is at the top of the downcomer. In some embodiments, two different gas composition zones in a multizone circulating reactor. In some embodiments, make-up monomers, comonomers, molecular weight regulators, and/or inert fluids are introduced at any point of the downcomer. In some embodiments, these components are introduced below the barrier feeding point. In some embodiments, the molecular weight regulator is hydrogen. In some embodiments, varying monomer, comonomer and hydrogen concentrations are established along the downcomer, thereby further differentiating the polymerization conditions.

In some embodiments, the gas-phase polymerizations are carried out at temperatures from 20 to 200° C., alternatively from 30 to 160° C., alternatively from 65 to 125° C. In some embodiments, the polymerization pressures for preparing the ethylene polymers are from 0.5 MPa to 10 MPa, alternatively from 1.0 MPa to 8 MPa, alternatively from 1.5 MPa to 4 MPa. As used herein, the term "pressure" refers to absolute pressure and has the dimension MPa (abs).

In some embodiments, the process is carried out in the presence of a reaction gas made from or containing propane as polymerization diluent. In some embodiments, the reaction gas mixture within the reactor is further made from or containing the olefins to be polymerized, that is, ethylene and one or more optional comonomers. In some embodiments, the reaction gas mixture has a content of inert components from 30 to 99 vol. %, alternatively from 50 to 95 vol. %, alternatively from 60 to 90 vol. %. In some embodiments, the reaction gas mixture is further made from or containing additional components such as antistatic agents or molecular weight regulators. In some embodiments, the molecular weight regulator is hydrogen. In some embodiments, the components of the reaction gas mixture are fed into the gas-phase polymerization reactor in gaseous form or as liquid which vaporizes within the reactor. In some embodiments, the polymerization is carried out in a condensing or super-condensing mode, wherein part of the circulating gas is cooled to below the dew point and returned to the reactor separately as a liquid and a gas phase or together as a two-phase mixture to make additional use of the enthalpy of vaporization for cooling the reaction gas.

In some embodiments, the process is carried out in a reactor cascade of two or more gas-phase polymerization reactors which includes a first polymerization reactor, into which the pre-activated polymerization catalyst is fed, and one or more subsequent polymerization reactors, which receive the polymerization catalyst fed to the first polymerization reactor in active form incorporated in ethylene polymer particles formed in the preceding reactors. In some embodiments, the gas-phase polymerization reactors of the reactor cascade are any kind of gas-phase polymerization reactors. In some embodiments, the gas-phase polymerization reactors are horizontally or vertically stirred gas-phase reactors, multizone circulating reactors, or fluidized-bed reactors. In some embodiments, the gas-phase polymerization reactors of the reactor cascade are of the same type. In some embodiments, the gas-phase polymerization reactors of the reactor cascade are different types of gas-phase polymerization reactors. In some embodiments, the gas-phase polymerization in the reactor cascade is preceded by a pre-polymerization stage. In some embodiments, the pre-polymerization stage is carried out as suspension polymerization. In some embodiments, the pre-polymerization stage is carried out in a loop reactor. In some embodiments, the polymerization is carried out in a reactor cascade having a fluidized-bed reactor as first reactor and, arranged downstream thereof, a multizone circulating reactor.

In some embodiments, fluidized-bed reactors employed as first polymerization reactors in reactor cascades for carrying out the process are equipped with a discharge pipe for discharging the ethylene polymer particles from the fluidized-bed reactors. In some embodiments, the discharge pipe is positioned such that the discharge pipe's upper opening is integrated into the distribution grid. In some embodiments, the discharge pipe is arranged vertically. In some embodiments, the fluidized-bed reactors equipped with such discharge pipes are as described in Patent Cooperation Treaty Publication No. WO 2013/083548 A2. In such fluidized-bed reactors, ethylene polymer particles coming from the fluidized bed fall into the discharge pipe due to gravity and form therein a densified bed of ethylene polymer particles. At the lower end of the discharge pipe, ethylene polymer particles are withdrawn and transferred to the subsequent gas-phase reactor. Consequently, the ethylene polymer particles within the discharge pipe move downwards from top to bottom of the discharge pipe driven by gravity. In some embodiments, the ethylene polymer particles move as plug flow from top to bottom of the discharge pipe. At the discharge pipe's lower end, the discharge pipe is provided with a discharge valve through which the ethylene polymer particles are withdrawn from the discharge pipe. Propane is fed into the discharge pipe in an amount that an upward stream of propane is induced in the bed of ethylene polymer particles above the propane introduction point. In some embodiments, the propane is introduced into the lower third of the discharge pipe. In some embodiments, the propane is introduced at a position near the lower end of the discharge pipe. In some embodiments, the propane is fed at more than one position into the discharge pipe. In some embodiments, the propane is fed such that the propane is distributed over the whole cross-section of the discharge pipe in a region above the propane introduction point. In some embodiments, the propane is fed in gaseous form into the discharge pipe. Accordingly, the introduced propane replaces the reaction gas of the fluidized-bed reactor and acts as barrier, thereby preventing the reaction gas of the fluidized-bed reactor from being transferred to the second polymerization reactor. By utilizing purified propane made from or containing no more than a minor amount of unsaturated components such as propylene, a noticeable polymerization does not occur in the discharge pipe and/or in the transfer line from the fluidized-bed reactor to the second gas-phase polymerization reactor which cause operational problems the discharge pipe in the transfer of polyethylene particles from a first to a second polymerization reactor such as a blockage of the discharge pipe and/or the ethylene polymer transfer line.

In some embodiments, the ethylene polymers obtained in the process are multimodal. As used herein, the term "multimodal" refers to polymers made from or containing multiple polymer components, wherein each component is produced in a separate reactor or reactor zone and differing from the other component(s) regarding type and/or amount of comonomer, or molecular weight distribution. As used herein, the term "multimodal" includes also "bimodal".

Figure 1:
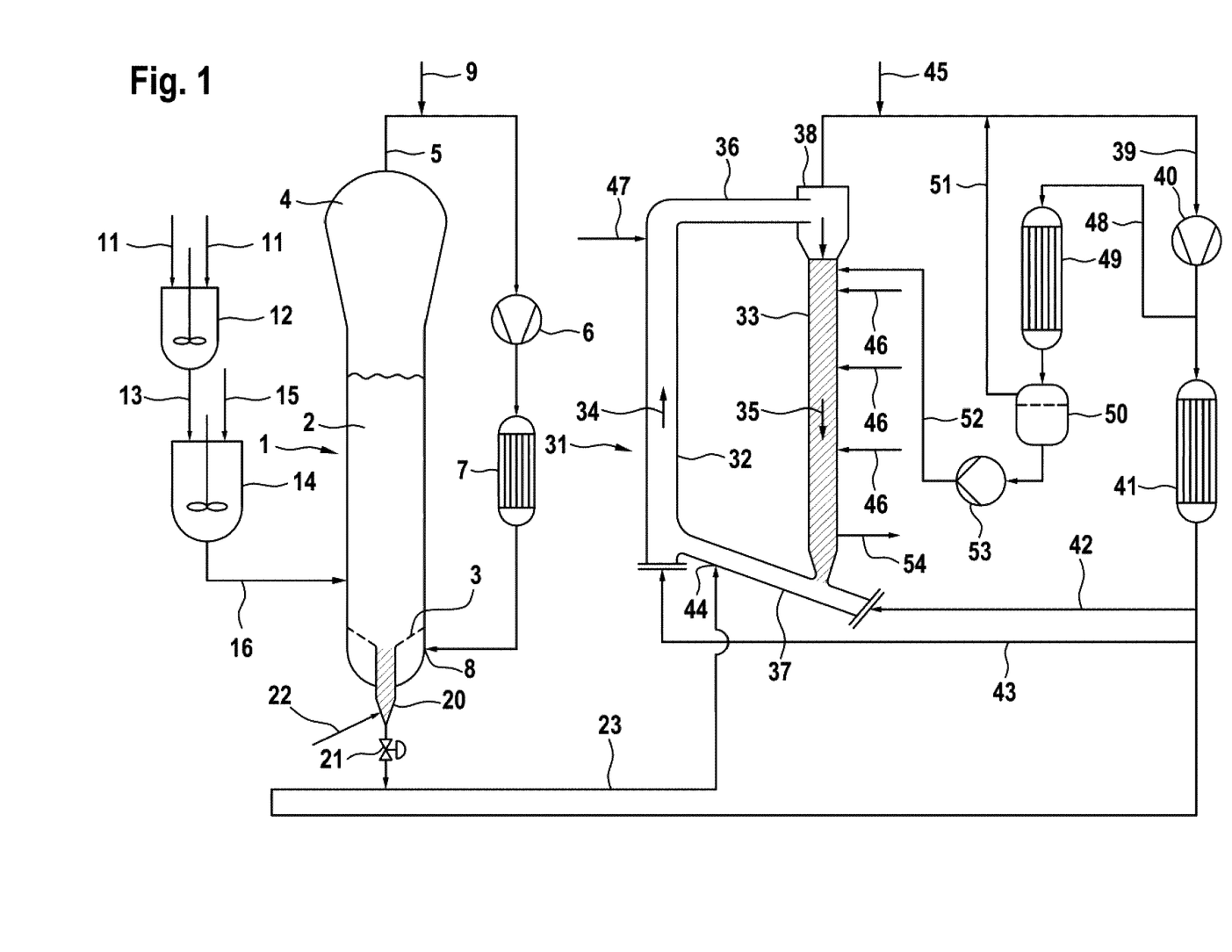
FIG. 1 is a schematic showing a set-up of a polymerization reactor cascade for preparing an ethylene polymer.

In some embodiments, the multimodal ethylene polymers are prepared in a cascade of polymerization reactors or reactor zones operated under different polymerization conditions and the final polymer is a mixture of the different polymers produced in the respective reactors or reactor zones. Catalyst and polymer is transferred from reactor to reactor in series. In some embodiments and as shown in FIG. 1, the pre-activated catalyst is fed to the first reactor of the cascade of two gas-phase reactors, along with ethylene, propane, an organometallic compound as cocatalyst, and optionally hydrogen and/or comonomer. The polymer exiting the first reactor results from the catalyst activity and selectivity in that reactor, which in turn is linked to the quantity of organometallic compound present, the reactor temperature, pressure, and feed concentrations. However, the catalyst activity and selectivity of the catalyst in the first reactor is affected by the interaction of the catalyst, organometallic compound cocatalyst and catalyst poisons present. If catalyst poisons enter the reactors, the poisons chemically react with the organometallic compound, thereby changing the quantity of the organometallic compound present. In some embodiments, the catalyst poisons enter with the propane stream. In some embodiments, the resulting quantity of organometallic compound present changes the activity and selectivity of the catalyst system.

In the second and any subsequent reactors, the same interaction occurs between impurities entering with the propane, active catalyst in the polymer, and organometallic compound cocatalyst, except that no fresh organometallic compound and no additional polymerization catalyst are added. Instead, the reactors receive the active catalyst within the ethylene polymer particles and the cocatalyst from the preceding reactor. Therefore, in multi-reactor cascade systems, while polymerization of ethylene occurs in each of the dedicated reactors to make polymers, each resulting polymer having the polymer's own molecular weight, the activity of the catalyst and concentration of the organometallic compound cocatalyst changes within each reactor, and from reactor to reactor. It is believed that the complexity of such systems increases as the number of reactors increase. Different from polyethylene grades produced in a single reactor, the polymerization products of multi-reactor polymerization units are the result of at least two polymerizations that target individual polymers in each reactor or reactor zone to achieve a final product property set for the final polymer. In some embodiments and in case of preparing multimodal ethylene polymers, for which a different ethylene polymer is produced in the polymerization reactors or reactor zones, small differences in the structure and composition of the ethylene polymer fractions produced in the individual polymerization reactors or reactor zones result in notable differences in the product properties of the final ethylene polymer.

In some embodiments, the ethylene polymers produced by the polymerization process are high density polyethylene (HDPE) resins. In some embodiments, the high density polyethylene resins have a density within the range of from 0.935 g/cm$^3$ to 0.970 g/cm$^3$, alternatively from 0.940 g/cm$^3$ to 0.970 g/cm$^3$, alternatively of 0.945 g/cm$^3$ to 0.965 g/cm$^3$. Density is measured according to DIN EN ISO 1183-1:2004, Method A (Immersion) with compression molded plaques of 2 mm thickness which were prepared with a defined thermal history: Pressed at 180° C., 20 MPa for 8 min with subsequent crystallization in boiling water for 30 min.

In some embodiments, the HDPE resin has a melt flow rate $MFR_{21.6}$ from 1 g/10 min to 100 g/10 min, alternatively from 1.5 g/10 min to 50 g/10 min, alternatively from 2 g/10 min to 35 g/10 min. The $MFR_{21.6}$ is measured according to DIN EN ISO 1133:2005, condition G at a temperature of 190° C. under a load of 21.6 kg.

In some embodiments, the ethylene polymers produced by the polymerization process are used for preparing films, pipes or small blow molding or large blow molding polyethylene articles. In some embodiments, the films, pipes or small blow molding or large blow molding polyethylene articles are prepared by converting the ethylene polymer to a film, pipe or small blow molding or large blow molding polyethylene article.

FIG. 1 is a schematic showing a set-up of a polymerization reactor cascade having a fluidized-bed reactor and a multizone circulating reactor for carrying out the process of the present disclosure.

The first gas-phase reactor, fluidized-bed reactor (1), has a fluidized bed (2) of polyethylene particles, a gas distribution grid (3) and a velocity reduction zone (4). In some embodiments, the velocity reduction zone (4) is of increased diameter compared to the diameter of the fluidized-bed portion of the reactor. The polyethylene bed is kept in a fluidization state by an upwardly flow of gas fed through the gas distribution grid (3) placed at the bottom portion of the reactor (1). The gaseous stream of the reaction gas leaving the top of the velocity reduction zone (4) via recycle line (5) is compressed by compressor (6), transferred to a heat exchanger (7), wherein the gaseous stream is cooled, and then recycled to the bottom of the fluidized-bed reactor (1) at a point below the gas distribution grid (3) at position (8). In some embodiments, make-up monomers, molecular weight regulators, and propane are fed into the reactor (1) at various positions. In some embodiments, the make-up monomers, molecular weight regulators, and propane are fed into the reactor (1) via line (9) upstream of the compressor (6).

For activating the polymerization catalyst system utilized in the polymerization process of the present disclosure, a solid catalyst component, a cocatalyst such as an aluminum alkyl compound, and optionally an external electron donor compound are fed together with propane as a liquid diluent via one or more lines (11) to a first continuously operated stirred tank (12), wherein the components are contacted. The content of stirred tank (12) is transferred via line (13) to a second continuously operated stirred tank (14). In some embodiments, further components are added via one or more lines (15) to the second stirred tank (14). In some embodiments, the further components are made from or containing additional propane. In some embodiments, additionally ethylene or a mixture of ethylene and one or more 1-olefins are introduced into the second stirred tank (14) for carrying out a pre-polymerization. The content of the second stirred tank (14) is transferred to fluidized-bed reactor (1) via line (16).

The fluidized-bed reactor (1) further has a discharge pipe (20), which is integrated with the discharge pipe's upper opening into the gas distribution grid (3). In some embodiments, the discharge pipe is arranged vertical. In some embodiments, the discharge pipe (20) has a uniform diameter. In some embodiments, the discharge pipe (20) has more sections having decreasing diameters in the downward direction. In some embodiments, the gas distribution grid (3) is flat. In some embodiments, the gas distribution grid (3) has a cone shape such that the gas distribution grid's downward inclination towards the discharge pipe (20) fosters the entry of the polyethylene particle into the discharge pipe (20) due to gravity. In some embodiments, the upper opening of the discharge pipe (20) is in a central position with respect to the gas distribution grid (3).

During operation of fluidized-bed reactor (1), the discharge pipe (20) contains a bed of polyethylene particles which moves from top to bottom of the discharge pipe. The polyethylene particles enter the discharge pipe (20) through the upper opening. In some embodiments, the polyethylene particles are withdrawn continuously through discharge valve (21). In some embodiments, discharge valve (21) is a segmental ball valve.

Propane is fed via line (22) into the discharge pipe (20). In some embodiments, the propane is fed at a position near the lower end of the discharge pipe in an amount that an upward stream of the propane is induced in the bed of polyethylene particles. Discharge valve (21) is arranged above a transfer line (23) for transferring the polyethylene particles to a second gas-phase reactor.

The second gas-phase reactor is a multizone circulating gas-phase reactor (31) with two reaction zones, riser (32) and downcomer (33), which are repeatedly passed by the polyethylene particles. Within riser (32), the polyethylene particles flow upward under fast fluidization conditions along the direction of arrow (34). Within downcomer (33), the polyethylene particles flow downward under the action of gravity along the direction of arrow (35). The riser (32) and the downcomer (33) are interconnected by the interconnection bends (36) and (37).

After flowing through the riser (32), the polyethylene particles and the gaseous mixture leave the riser (32) and are conveyed to a solid/gas separation zone (38). In some embodiments, this solid/gas separation is effected by a separation device. In some embodiments, the separation device is a centrifugal separator like a cyclone. From the separation zone (38), the polyethylene particles enter the downcomer (33).

The gaseous mixture leaving the separation zone (38) is recycled to the riser (32) by a recycle line (39), equipped with a compressor (40) and a heat exchanger (41). Downstream of the heat exchanger (41), the recycle line (39) splits and the gaseous mixture is divided into three separated streams: line (42) conveys a part of the recycle gas into the interconnection bend (37), line (43) conveys another part the recycle gas to the bottom of the riser (32), thereby establishing fast fluidization conditions therein, and a further part of the recycle gas is conveyed through transfer line (23) for transferring the polyethylene particles obtained in fluidized-bed reactor (1) into multizone circulating gas-phase reactor (31). The polyethylene particles coming from the first gas-phase reactor enter the multizone circulating gas-phase reactor (31) at the interconnection bend (37) in position (44).

In some embodiments, make-up monomers, make-up comonomers, and optionally inert gases or process additives are fed to the multizone circulating reactor (31) via one, two or more lines (45) or (46), placed at any point of the gas recycle line (39) or the downcomer (33). In some embodiments, process additives such as antistatic agents are fed via line (47).

A part of the gaseous mixture leaving the separation zone (38) exits recycle line (39) after the compressor (40) and is sent through line (48) to heat exchanger (49) where the gaseous mixture is cooled to a temperature at which the monomers and the optional inert gas are partially condensed. A separating vessel (50) is placed downstream the heat exchanger (49). The separated gaseous mixture is recirculated through line (51) to recycle line (39) and the separated liquid is fed to the downcomer (33) through line (52) by pump (53).

The polyethylene particles obtained in the multizone circulating reactor (31) are continuously discharged from the bottom part of downcomer (33) via discharge line (54).

In some embodiments and in the process of the present disclosure, the degassing of the discharged ethylene polymer particles occurs in a first step with propane as gas for removing entrained parts of the reaction gas which have been discharged from the polymerization reactor together with the ethylene polymer particles as intergranular gas or as dissolved hydrocarbons. In some embodiments, this first degassing with propane is carried out in a first degassing vessel. In some embodiments, the separation of the ethylene polymer particles discharged from the polymerization reactor from the major part of the concomitantly discharged reaction gas is carried out together with or separately from the first degassing step of the ethylene polymer particles, either in terms of time or in terms of space. In some embodiments, the separation of the solid ethylene polymer particles from the major part of the reaction gas is carried out in a separation vessel and the polyolefin particles are thereafter transferred to the first degassing vessel for being contacted with a propane stream. In some embodiments, the separation vessel is operated at a pressure between the pressure in the polymerization reactor and the pressure in the first degassing vessel. In some embodiments, the ethylene polymer particles are directly discharged into the first degassing vessel, wherein the ethylene polymer particles are simultaneously separated from the major part of the concomitantly discharged reaction gas and contacted with the propane stream.

In some embodiments, the propane stream withdrawn from the first degassing vessel, which is enriched in unreacted ethylene and comonomers, oligomers and other hydrocarbons, is conveyed to a propane and monomer work-up unit, wherein the gas mixture is separated in fractions. In some embodiments, the separated fractions are recycled to the polymerization process in worked-up form. In some embodiments, the ethylene polymer particles are discharged with first separating the ethylene polymer particles from the major part of the concomitantly discharged reaction gas before transferring the ethylene polymer particles into the first degassing vessel, the gas stream withdrawn from the separation vessel is combined with the propane stream withdrawn from the first degassing vessel, and the combined streams are conveyed to the propane and monomer work-up unit. In some embodiments, the degassing and work-up processes are as described in Patent Cooperation Treaty Publication No. WO 2006/082007 A1, Patent Cooperation Treaty Publication No. WO 2014/090860 A1 or Patent Cooperation Treaty Application No. PCT/EP2018/071031.

In some embodiments, the propane and monomer work-up unit produces a liquid stream which is recycled to a polymerization unit. In some embodiments, the propane and monomer work-up unit produces one or more liquid streams and one or more gaseous streams by working up the gas mixture. In some embodiments, one or more of the liquid streams which are recycled to a polymerization unit are evaporated before being recycled to the polymerization unit. In some embodiments, the propane and monomer work-up unit use a method for separating the propane from higher molecular weight or lower molecular weight components. In some embodiments, the separation techniques are distillation or condensation. In some embodiments, the separation technique is distillation. In some embodiments, the propane and monomer work-up unit has two separation stages, a separation stage primarily for separating the propane from higher molecular weight gas components, and a separation stage primarily for separating the propane from lower molecular weight gas components. In some embodiments, the higher molecular weight gas components are higher molecular weight alkanes or higher molecular weight olefins. In some embodiments, the higher molecular weight alkanes are selected from the group consisting of butane, hexane and octane. In some embodiments, the higher molecular weight olefins are selected from the group consisting of 1-butene, 1-hexene and 1-octene. In some embodiments, the lower molecular weight gas components are selected from the group consisting of ethane, ethylene, hydrogen and nitrogen. In some embodiments, the gas stream first passes the separation stage for separating the propane from higher molecular weight gas components or the gas stream passes the separation stage for separating propane from lower molecular weight gas components. In some embodiments, the gas stream first passes the separation stage for separating the propane from higher molecular weight gas components.

In some embodiments, the solvent for additives is liquid propane received from the propane and monomer work-up unit. In some embodiments, the additives are added to the polymerization process in dissolved form. In some embodiments, the additives are antistatic agents.

In some embodiments, the propane and monomer work-up unit is designed to recover the components of the gas mixture and to recycle these components to the gas-phase polymerization unit. In some embodiments, a large portion of the reaction gas used in the polymerization is recycled. In some embodiments, some losses occur. In some embodiments, these lost amounts are replaced by a fresh feed.

For replacing losses of propane from the polymerization unit, a feed stream of fresh propane is fed to the gas-phase polymerization unit. In some embodiments, the propane employed as polymerization diluent contains impurities. In some embodiments, a non-purified propane stream contains a variety of impurities. In some embodiments and depending on the source of the propane, the quality of the propane feed prior to purification varies in amount and composition of the impurities. In some embodiments, the quality varies with time. In some embodiments, the quality varies based on a change of the propane source or fluctuations in the propane production process.

In some embodiments, the impurities of non-purified propane are selected from the group consisting of hydrogen; oxygen; carbon monoxide; carbon dioxide; hydrocarbons having oxygen-containing functional groups; water; sulfur-containing compounds; nitrogen-based molecules; or arsine; or mixtures thereof. In some embodiments, the hydrocarbons having oxygen-containing functional groups are selected from the group consisting of alcohols, glycols, phenols, ethers, and carbonyl compounds. In some embodiments, the carbonyl compounds are selected from the group consisting of ketones, aldehydes, carboxylic acids, esters, and fatty acids. In some embodiments, the sulfur-containing compounds are selected from the group consisting of sulfur dioxides and trioxides, hydrogen sulfide ($H_2S$), carbonyl sulfide (COS), and mercaptans. In some embodiments, the nitrogen-based molecules are selected from the group consisting of ammonia, amines, and nitrites. In some embodiments, the impurities are saturated hydrocarbons; alkenes; alkynes; or dienes. In some embodiments, the hydrocarbons are selected from the group consisting of methane, ethane, and butane. In some embodiments, the alkene is propylene. In some embodiments, the alkyne is acetylene. In some embodiments, the dienes are selected from the group consisting of 1,3-butadiene and propadiene.

In some embodiments, the feed stream for replacing losses of propane from the polymerization unit is a purified propane stream, where the purification has been carried out by passing a hydrocarbon stream through hydrocarbon purification units which reduce at least the concentration of propylene, acetylene, carbon monoxide, carbon dioxide, oxygen and water contained in the hydrocarbon stream. In some embodiments, the purified propane stream is made from or containing at least 99% mol propane and not more than 100 ppm-mol propylene, alternatively from 0.01 to 75 ppm mol propylene.

In some embodiments, the purified propane feed stream fed to the gas-phase polymerization unit is made from or containing not more than 0.03 ppm-mol carbon monoxide, alternatively not more than 0.01 ppm-mol carbon monoxide; not more than 0.4 ppm-mol carbon dioxide, alternatively not more than 0.2 ppm-mol carbon dioxide; not more than 2.0 ppm-mol oxygen, alternatively not more than 1.0 ppm-mol oxygen; not more than 3.0 ppm-mol acetylene, alternatively not more than 1.0 ppm-mol acetylene; and not more than 2.0 ppm-mol water, alternatively not more than 1.0 ppm-mol water.

In some embodiments, passing the propane feed stream through the hydrocarbon purification units reduces the total quantity of impurities in the stream and ensures that the level of impurities dosed to the polymerization is kept constant. In some embodiments, the conditions for the catalyst pre-activation and in the polymerization reactors are rendered stable. In some embodiments, variations of the concentration of organometallic compounds in the polymerization reactor(s) and variations of catalyst sensitivity are controlled.

In some embodiments, one of the hydrocarbon purification units for preparing the purified propane stream is a catalytic hydrogenation unit. As used herein, the term "catalytic hydrogenation" refers to a chemical reaction wherein unsaturated chemical compounds such as propylene are reacted with hydrogen in the presence of a hydrogenation catalyst to saturated chemical compound such as propane. In some embodiments, the employed catalyst is a catalyst based on platinum, palladium, rhodium or transition metals such as molybdenum, tungsten, chromium or iron, cobalt, copper and nickel. In some embodiments, the catalysts are used individually or in a mixture. In some embodiments, the catalysts are applied to a support such as alumina, silica-alumina, activated carbon, or ceramics. In some embodiments, the hydrogenation catalyst is a platinum- or palladium-based composition on an alumina support, alternatively platinum or palladium on alumina. In some embodiments, the catalysts are compositions made from or containing from 0.01 to 2 percent by weight of palladium on an alumina support.

In some embodiments and for achieving complete conversion of unsaturated chemical compounds in the catalytic hydrogenation unit, the concentration of propylene and other unsaturated components in the stream to be hydrogenated is below a threshold concentration. In some embodiments, propylene is converted to propane. In some embodiments, a part of the hydrogenated stream which has passed the catalytic hydrogenation unit is recycled to a position upstream of the catalytic hydrogenation unit and mixed with the stream to be hydrogenated for diluting this stream. In some embodiments and by adapting the ratio of the fresh stream made from or containing propylene and the recycled stream having already passed the catalytic hydrogenation unit, the concentration of unsaturated components in the stream entering the catalytic hydrogenation unit is adjusted.

In some embodiments, the purification of the propane feed stream occurs by subsequently passing various purification units. In some embodiments, the number and order of the purification units vary. In some embodiments, one of the purifications units is a catalytic hydrogenation unit. In some embodiments, the hydrocarbon feed stream to be purified in the sequential passed purification units is provided in liquid form.

In some embodiments, the purification of the propane feed stream occurs by subsequently passing a hydrocarbon stream through four purification units prior to feeding the purified stream to the gas-phase polymerization unit. In some embodiments, the first purification unit is a unit for reacting impurities in the hydrocarbon stream with a Cu based catalyst to remove COS, $H_2S$ and arsine from the hydrocarbon stream. In some embodiments, the second purification unit is a unit for catalytically hydrogenating the stream coming from the first purification unit. In some embodiments, the third purification unit is a unit for separating propane from higher molecular weight or lower molecular weight components. In some embodiments, the fourth purification unit is a drying unit.

In some embodiments, the catalyst employed in the first purification unit is a catalyst made from or containing Cu and Zn, and optionally a promoter and a support. In some embodiments, the catalyst, in reduced form, is obtained by treating with hydrogen, alternatively in a hydrogen atmosphere, at a temperature 80 to 180° C. and at a pressure of 1 to 50 bar. In some embodiments, the copper is at least partly present as Cu, in metallic form. A catalyst is made from or containing:

25 to 50% wt., alternatively 35 to 45% wt. CuO;
30 to 65% wt., alternatively from 35 to 45% wt ZnO;
5 to 40% wt., alternatively 20 to 30% wt. of Al2O3, SiO2, TiO2, MgO, iron oxides or mixtures thereof; and
0 to 5% wt, alternatively 0 to 1% wt, of promoters.

In some embodiments, the promoters are selected from the group consisting of potassium, sodium, manganese, chromium, cobalt, tungsten, molybdenum, nickel, iron, magnesium, calcium and mixtures thereof. In some embodiments, the reduced form of the catalyst is obtained in situ, that is, by mixing hydrogen into the monomer stream to be purified.

In some embodiments, the second purification unit is a unit for catalytically hydrogenating the stream coming from the first purification unit.

In some embodiments, the third purification unit is a separation unit for separating higher molecular weight or lower molecular weight components from the propane stream coming from the second purification unit, alternatively a distillation unit. In some embodiments, the third purification unit has two separation stages, a separation stage primarily for separating the propane from higher molecular weight gas components, and a separation stage primarily for separating the propane from lower molecular weight gas components. In some embodiments, the higher molecular weight gas components are higher molecular weight alkanes. In some embodiments, the higher molecular weight alkanes are selected from the group consisting of butane, hexane and octane. In some embodiments, the lower molecular weight gas components are selected from the group consisting of ethane, ethylene, hydrogen and nitrogen. In some embodiments, the propane stream first passes the separation stage for separating the propane from higher molecular weight gas components or the gas stream first passes the separation stage for separating propane from lower molecular weight gas components. In some embodiments, the gas stream first passes the separation stage for separating the propane from lower molecular weight gas components.

In some embodiments, the fourth purification unit is a drying unit for removing water and remaining polar impurities by adsorption on a desiccant. In some embodiments, the water-reduction catalysts are molecular sieves. Molecular sieves are synthetically-produced zeolites, a crystalline form of alkali metal aluminosilicates, and have high structural consistency. In some embodiments, the zeolites are activated to obtain adsorbent properties by eliminating hydration water. The resulting material is porous with an affinity for water, specific gases and liquids. In some embodiments and in the fourth purification unit, water and remaining polar impurities react with the molecular sieve, where the water and the remaining polar impurities are adsorbed by the molecular sieve. In some embodiments, the fourth purification unit has a closed vessel which is constructed of materials consistent with the temperature and pressure of the fourth purification unit product stream, and which is arranged to house the water-reduction catalyst and to distribute the flow of the fourth purification unit product stream, thereby achieving contact with the water-reduction catalyst. The propane stream becomes depleted in water concentration and concentration of remaining polar impurities as the stream progresses through the vessel.

In some embodiments, the purification of the propane feed stream occurs by subsequently passing a hydrocarbon stream through a different combination of four purification units prior to feeding the purified stream to the gas-phase polymerization unit. In some embodiments, the first purification unit is a unit for removing oxygen and carbon monoxide from the hydrocarbon stream by a reduced Cu based catalyst. In some embodiments, the second purification unit is a drying unit. In some embodiments, the third purification unit is a unit for removing COS, $H_2S$ and arsine by a Cu based catalyst from the stream coming from the second purification unit. In some embodiments, the fourth purification unit is a unit for catalytically hydrogenating the stream coming from the third purification unit.

In some embodiments, the propane feed stream, which is fed to the gas-phase polymerization unit, is passed through hydrocarbon purification units and the ethylene and the $C_4$-$C_{12}$-1-alkenes, which are fed as comonomer to at least one of the polymerization reactors, are first passed through hydrocarbon purification units, thereby reducing at least the concentration of carbon monoxide, carbon dioxide, oxygen, acetylene and water contained in the olefins, before being fed to the polymerization unit.

Figure 2:
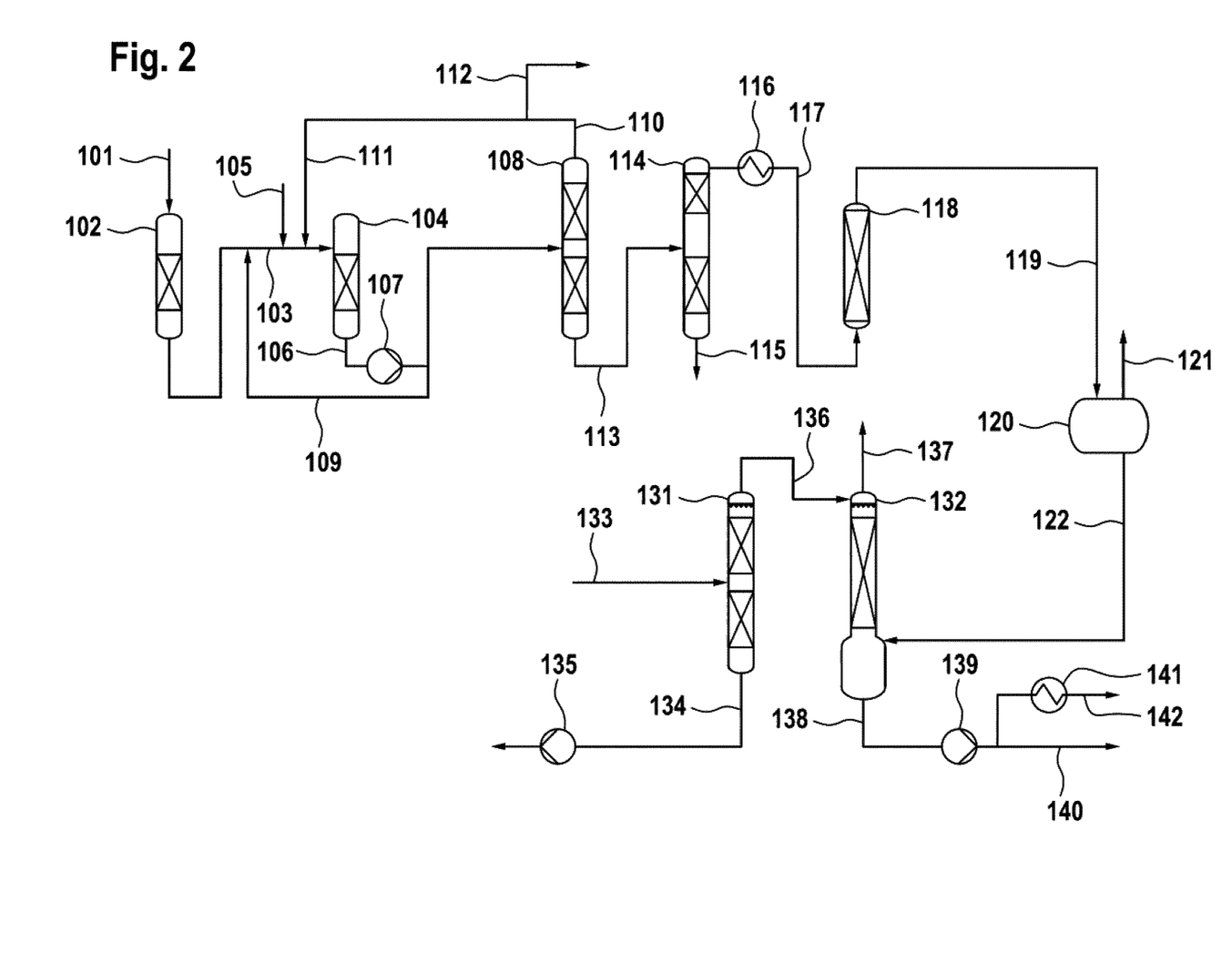
FIG. 2 is a schematic showing a set-up of hydrocarbon purification units for purifying a propane feed stream and of a propane and monomer work-up unit for recovering components of the reaction gas discharged from a polymerization reactor.

FIG. 2 is a schematic showing a setup of hydrocarbon purification units for purifying a propane feed stream and of a propane and monomer work-up unit for recovering components of the reaction gas discharged from the polymerization reactor.

A liquid stream made from or containing propane and impurities is provided via line (101) to a first propane purification vessel (102) made from or containing a catalyst made from or containing Cu, Zn, and a support material for removing sulfur containing impurities from the propane stream. The resulting stream is transferred via line (103) to a second propane purification vessel (104) made from or containing a catalytic hydrogenating catalyst for hydrogenating unsaturated chemical compound such as propylene to saturated chemical compound such as propane. The hydrogen needed for the hydrogenation is added via line (105). The hydrogenated propane stream is withdrawn from the bottom of the second propane purification vessel (104) via line (106) and transferred by a pump (107) to a first separation column (108). In some embodiments and for being able to maintain the temperature within the second propane purification vessel (104), the concentration of propylene and other unsaturated components in the stream entering the second propane purification vessel (104) is reduced by recycling a part of the hydrogenated propane stream withdrawn from the second propane purification vessel (104) via line (109) and combining this recycled part with the propane stream coming from the first propane purification vessel (102).

In the first separation column (108), lower molecular weight components are separated from the propane stream entering column (108) and withdrawn from the top of column (108) via line (110). In some embodiments, this gas withdrawn via line (110), which is made from or containing non-reacted hydrogen which has passed the second propane purification vessel (104), is recycled to the second propane purification vessel (104) via line (111) or is purged as off-gas via line (112). The propane stream freed from the lower molecular weight gas components is transferred via line (113) to a second separation column (114). In the second separation column (114), higher molecular weight components are separated from the propane stream entering column (114) and withdrawn from the bottom of column (114) via line (115). In some embodiments, this liquid withdrawn via line (115), which is made from or containing the higher molecular weight gas components, is purged after evaporation as off-gas. The propane stream freed from the higher molecular weight components passes a heat-exchanger (116) for being liquified and is transferred via line (117) to the bottom of a third propane purification vessel (118) having a desiccant for removing water and remaining polar impurities. The purified propane stream is withdrawn from the top of the third propane purification vessel (118) and transferred via line (119) to a propane storage tank (120).

For recovering propane, ethylene and comonomers from the reaction gas discharged from the polymerization reactor or the combination of polymerization reactors and/or from the gas mixture coming from a first degassing vessel, FIG. 2 shows a propane and monomer work-up unit have two propane distillation columns (131) and (132). The combined streams of gas discharged from the polymerization reactor(s) and gas coming from a first degassing vessel are introduced via line (133) into the first propane distillation column (131), wherein higher molecular weight components are separated from the propane stream entering column (131). In some embodiments, the higher molecular weight components, which are made from or containing the comonomers used in the polymerization, are withdrawn from the bottom of the first propane distillation column (131) via line (134) in liquid form and pumped back to the polymerization unit by pump (135). The gas stream freed from the higher molecular weight components is withdrawn from the top of the first propane distillation column (131) via line (136) and transferred into the second propane distillation column (132). In some embodiments, lower molecular weight components of the gas introduced into the second propane distillation column (132), which include ethylene, are withdrawn from the top of the second propane distillation column (132) via line (137) and recycled to the polymerization process or purged as off-gas. Recovered propane freed from lower molecular weight components and from higher molecular weight components is withdrawn from the second propane distillation column (132) in liquid form via line (138). In some embodiments, the propane withdrawn from the second propane distillation column (132) via line (138) is transferred back to the polymerization process by pump (139), either in liquid form via line (140) or, after being evaporated in heat-exchanger (141), via line (142).

In some embodiments, the purified fresh propane collected in storage tank (120) is transferred directly to the polymerization process via line (121). In some embodiments, the purified fresh propane is transferred via line (121) to dedicated positions of the gas-phase polymerization unit. In some embodiments, the purified fresh propane is combined with the recovered propane obtained in the propane and monomer work-up unit by being transferred via line (122) into the second propane distillation column (132).

In some embodiments, the propane used as liquid diluent for pre-activating the polymerization catalyst is taken from the purified propane feed stream. In some embodiments, the whole purified propane feed stream for replacing losses of propane from the polymerization unit is fed to the pre-activation vessel(s). In some embodiments, a part of the purified propane feed stream is transferred as liquid diluent for pre-activating the polymerization catalyst to a pre-activation vessel and the remainder of the purified propane feed stream is introduced into the gas-phase polymerization unit at one or more different positions. In some embodiments, the remainder of the purified propane feed stream is transferred to the propane and monomer work-up unit for being introduced into the gas-phase polymerization unit.

In some embodiments, the purification of the propane feed stream, which is fed to the gas-phase polymerization unit, occurs directly before feeding the propane to the gas-phase polymerization unit. In some embodiments, the hydrocarbon purification units are installed at the same site as the gas-phase polymerization unit.

In some embodiments, the purification of the propane and the ethylene polymerization or copolymerization are locally and timely separated. In some embodiments, high-purity propane, which is made from or containing at least 99% mol propane and not more than 100 ppm-mol propylene and which had passed hydrocarbon purification units which reduce at least the concentration of propylene, acetylene, carbon monoxide, carbon dioxide, oxygen and water in a hydrocarbon stream which passes the hydrocarbon purification units, is supplied to the site of the gas-phase polymerization unit.

In some embodiments, the hydrocarbon stream for preparing the purified propane stream is a purified propylene stream made from or containing at least 99 mol % propylene. In some embodiments, the purification and the hydrogenation of the propylene occur in separated stages.

EXAMPLES

The melt flow rate $MFR_{21.6}$ was determined according to DIN EN ISO 1133-1:2012-03 at a temperature of 190° C. under a load of 21.6 kg.

The melt flow rate $MFR_5$ was determined according to DIN EN ISO 1133-1:2012-03 at a temperature of 190° C. under a load of 5 kg.

The melt flow rate $MFR_{2.16}$ was determined according to DIN EN ISO 1133-1:2012-03 at a temperature of 190° C. under a load of 2.16 kg.

The Flow Rate Ratio FRR is the ratio of $MFR_{21.6}/MFR_5$.

The density was determined according to DIN EN ISO 1183-1:2004, Method A (Immersion) with compression molded plaques of 2 mm thickness. The compression molded plaques were prepared with a defined thermal history: pressed at 180° C., 20 MPa for 8 min with subsequent crystallization in boiling water for 30 min.

The swell ratio was measured in a high-pressure capillary rheometer (Rheograph25, Göttfert Werkstoff-Prüfmaschinen GmbH, Buchen, Germany) at a shear rate of 1440 s$^{-1}$ in a 30/2/2/20 round-perforation die with conical inlet (angle=20°, D=2 mm, L=2 mm, total length=30 mm) at a temperature of 190° C., using a laser-diode placed at a distance of 78 mm from the die exit. The extrudate was cut (by an automatic cutting device from Göttfert) at a distance of 150 mm from the die-exit, at the moment the piston reaches a position of 96 mm from the die-inlet. Swell ratio (SR) [%] is defined as difference $(d_{max}-d_d)\times 100$ divided by $d_d$ with $d_{max}$ being the maximum diameter of the strand and $d_d$ being the diameter of the die; $SR=(d_{max}-d_d)\ 100\%/d_d$.

The comonomer content was determined by means of IR in accordance with ASTM D 6248 98, using an FT-IR spectrometer Tensor 27 from Bruker, calibrated with a chemometric model for determining ethyl or butyl side-chains in PE for 1-butene or 1-hexene as comonomer, respectively. The result was compared to the estimated comonomer content derived from the mass-balance of the polymerization process and found to agree.

The environmental stress cracking resistance was determined by a full notch creep test (FNCT) in accordance with international standard ISO 16770:2004 in aqueous surfactant solution. From the polymer sample, a compression molded 10 mm thick sheet was prepared. The bars with squared cross sections (10×10×100 mm) were notched using a razor blade on four sides perpendicularly to the stress direction. A notching device as described in M. Fleissner in Kunststoffe 77 (1987), pp. 45 was used for the sharp notch with a depth of 1.6 mm. The load applied was calculated from tensile force divided by the initial ligament area. Ligament area was the remaining area=total cross-section area of specimen minus the notch area. For FNCT specimen: $10\times 10\ mm^2-4$ times of trapezoid notch area=46.24 $mm^2$ (the remaining cross-section for the failure process/crack propagation). The test specimen was loaded using conditions as suggested by the ISO 16770 with constant load of 6 MPa at 50° C. in an aqueous solution of 2% by weight of ARKOPAL N100. The elapsed time until the rupture of the test specimen was detected.

The gel count was determined by preparing a cast film, analyzing the film defects by an optical scanning device and classifying and counting the film defects according to the defects' size (circle diameter). The films were prepared by an OCS extruder type ME 202008-V3 with 20 mm screw diameter and a screw length of 25 D with a slit die width of 150 mm. The cast line was equipped with a chill roll and winder (model OCS CR-9). The optical equipment consisted of a OSC film surface analyzer camera, model FTA-100 (flash camera system) with a resolution of 26 μm×26 μm. After purging the resin first for 1 hour to stabilize the extrusion conditions, inspection and value recording took place for 30 minutes. The resin was extruded at 220° C. with a take-off speed of about 2.7 m/min to generate a film with thickness 50 μm. The chill roll temperature was 70° C. The inspection of the prepared film with the surface analyzer camera provided the total content of gels and the content of gels with a diameter of more than 700 μm.

Example 1

The polymerization process was carried out under continuous conditions in a polymerization unit having two serially connected gas-phase reactors, a fluidized-bed reactor as the first reactor of the reactor cascade and a multizone circulating reactor having a riser and a downcomer as the subsequent polymerization reactor as shown in FIG. 1.

Propane Purification

The propane feed stream for replacing the propane losses in the polymerization process was a purified propane stream obtained by passing a liquid propane stream made from or containing propane and impurities as shown in Table 1 through four sequentially arranged purification units, which were installed near the gas-phase polymerization unit. The first unit contained a bed of a CuO/ZnO catalyst (PuriStar® R3-12 T5×3 obtained from BASF SE, Ludwigshafen, Germany) for removing COS, H2S, oxygen, carbon monoxide and carbon dioxide. The second unit was a catalytic hydrogenation unit containing a palladium-based catalyst (PuriStar R0-20 K2-4 obtained from BASF SE, Ludwigshafen, Germany) for hydrogenating propylene to propane. The third unit was a two-stage distillation unit for separating higher molecular weight or lower molecular weight components from the propane, and the fourth unit contained a 0.3 nm molecular sieve for removing water. The resulting purified liquid propane, which was directly transferred to the gas-phase polymerization unit, had the composition shown in Table 1.

Catalyst Preparation

For the preparation of the solid catalyst component, a magnesium chloride and alcohol adduct containing about 3 mols of alcohol was prepared following the method described in Example 2 of U.S. Pat. No. 4,399,054, but working at 2000 RPM instead of 10000 RPM. The adduct was subjected to a thermal treatment, under a nitrogen stream, over a temperature range of 50 to 150° C. until a weight content of 25% of alcohol was reached.

Into a 2 L four-necked round flask, purged with nitrogen, 1 L of $TiCl_4$ was introduced at 0° C. Then, at the same temperature, 70 g of a spherical MgCl2/EtOH adduct containing 25 wt. % of ethanol were added under stirring. The temperature was raised to 140° C. in 2 h and maintained for 120 minutes. Then, the stirring was discontinued. The solid product was allowed to settle. The supernatant liquid was siphoned off. The solid residue was then washed once with heptane at 80° C. and five times with hexane at 25° C. and dried under vacuum at 30° C.

Into a 260 $cm^3$ glass reactor provided with stirrer, 351.5 $cm^3$ of hexane at 20° C. and, while stirring, 7 g of the catalyst component were introduced at 20° C. Keeping constant the internal temperature, 5.6 $cm^3$ of tri-n-octylaluminum (TNOA) in hexane (about 370 g/l) and an amount of cyclohexylmethyl-dimethoxysilane (CMMS) to have molar ratio TNOA/CMMS of 50, were introduced into the reactor. The temperature was brought to 10° C. After 10 minutes stirring, 10 g of propylene were introduced into the reactor at the same temperature during a time of 4 hours. The consumption of propylene in the reactor was monitored, and the polymerization was discontinued when a theoretical conversion of 1 g of polymer per g of catalyst was deemed to be reached. Then, the whole content was filtered and washed three times with hexane at a temperature of 30° C. (50 g/l). After drying, the resulting pre-polymerized catalyst (A) was analyzed and found to contain 1.05 g of polypropylene per g of initial catalyst, 2.7% Ti, 8.94% Mg and 0.1% Al.

For supporting an internal electron donor on the pre-polymerized catalyst, about 42 g of the solid pre-polymerized catalyst component were charged in a glass reactor purged with nitrogen and suspended in 0.8 L of hexane at 50° C.

Then, ethyl acetate was carefully added dropwise (in 10 minutes) in an amount to have a molar ratio of 1.7 between Mg of the pre-polymerized catalyst and the organic Lewis base.

The suspension was kept under stirring for 2 h, with 50° C. as internal temperature.

Thereafter, the stirring was stopped and the solid was allowed to settle. A single hexane wash was performed at room temperature before recovering and drying the final catalyst.

Polymerization 13.8 g/h of the solid catalyst component with a molar feed ratio of electron donor/Ti of 8, were fed to a first stirred pre-activation vessel using 1 kg/h of the purified liquid propane coming from the four sequentially arranged purification units. Triisobutylaluminum (TIBA), diethylaluminum chloride (DEAC) and the electron donor tetrahydrofuran (THF) were also dosed into the first stirred pre-activation vessel. The weight ratio of triisobutylaluminum to diethylaluminum chloride was 7:1. The ratio of the aluminum alkyls (TIBA+DEAC) to the solid catalyst component was 5:1. The weight ratio of alkyls to THF was 70. The first pre-activation vessel was kept at 50° C. with a residence time of 30 minutes. The catalyst suspension of the first pre-activation vessel was continuously transferred to a second stirred pre-activation vessel, which was operated with a residence time of 30 minutes and kept also at 50° C. The catalyst suspension was then transferred continuously to fluidized-bed reactor (FBR) (1) via line (11).

In the first reactor, ethylene was polymerized using $H_2$ as molecular weight regulator and in the presence of propane as inert diluent. 50 kg/h of ethylene and 200 g/h of hydrogen were fed to the first reactor via line (9). No comonomer was fed to the first reactor.

The polymerization was carried out at a temperature of 80° C. and at a pressure of 2.9 MPa. The polymer obtained in the first reactor was discontinuously discharged via discharge pipe (20), separated from the gas into the stirred tank (12), and reintroduced into the second gas-phase reactor via line (23).

The polymer produced in the first reactor had a melt flow rate $MFR_{2.16}$ of 81 g/10 min and a density of 0.969 kg/dm³.

The second polymerization reactor was operated under polymerization conditions of about 80° C., and a pressure of 2.5 MPa. The riser had an internal diameter of 200 mm and a length of 19 m. The downcomer had a total length of 18 m, an upper part of 5 m with an internal diameter of 300 mm and a lower part of 13 m with an internal diameter of 150 mm. The second reactor was operated by establishing different conditions of monomers and hydrogen concentration within the riser (32) and the downcomer (33). The reactor conditions were achieved by feeding, via line (52), 330 kg/h of a liquid stream (liquid barrier) into the upper part of the downcomer (33). The liquid stream had a composition different from that of the gas mixture present in the riser. The liquid stream of line (52) came from the condensation step in the heat exchanger (49), at working conditions of 47° C. and 2.5 MPa, wherein a part of the recycle stream was cooled and partially condensed. 5 kg/h of propane, 50.8 kg/h of ethylene and 28 g/h of hydrogen were fed through lines (45) and (46) into the second reactor. In addition, 0.20 kg/h of 1-hexene were introduced into the downcomer (33) at a position located just below the barrier. The final ethylene polymer was discontinuously discharged via line (54). Of the final ethylene polymer discharged from the second reactor, around 49% by weight were produced in the first reactor (split 49:51).

Some further polymerization conditions in the polymerization reactors and the properties of the final ethylene polymer are shown in Table 2.

Example 2

The polymerization of Example 1 was repeated, however using a purified propane purified by the propane producer, which had a propane content of at least 99.95 vol. %. The propane was purchased from GHC Gerling, Holz & Co. Handels GmbH, Hamburg, Germany and had the composition shown in Table 1. The propane was supplied in cylinders at a pressure of 0.85 MPa(abs) and was fed to the first pre-activation vessel by a membrane pump.

The polymerization was carried out at the same reactor conditions as in Example 1. Some further polymerization conditions in the polymerization reactors and the properties of the final ethylene polymer are shown in Table 2.

Comparative Example A

The polymerization of Example 2 was repeated; however, a propane having a propane content of at least 99.5 vol. % was used. The propane was purchased from GHC Gerling, Holz & Co. Handels GmbH, Hamburg, Germany and had the composition shown in Table 1. The propane was supplied in cylinders at a pressure of 0.85 MPa(abs) and was fed to the first pre-activation vessel by a membrane pump.

To maintain a constant throughput of the reactor cascade, the catalyst feed was increased to 17.3 g/h of the solid catalyst component. The molar feed ratio of electron donor/Ti of 8 was maintained, while the feed of liquid propane to the first stirred pre-activation vessel was kept at 1 kg/h. To achieve the design density of the final ethylene polymer, the amount of 1-hexene fed to the downcomer (33) at the position located just below the barrier was reduced to 0.15 kg/h. Further polymerization conditions in the polymerization reactors and the properties of the final ethylene polymer are shown in Table 2.

TABLE 1

| | Example 1 | | | |
| --- | --- | --- | --- | --- |
| | before purification | after purification | Example 2 | Comparative Example A |
| propane [% mol] | >95.0 | >99.95 | >99.95 | >99.5 |
| propylene [ppm-mol] | 39 000 | 10 | 50 | 400 |
| acetylene [ppm-mol] | 400 | 1.0 | nil | nil |
| oxygen [ppm-mol] | nil | nil | 0.7 | 8 |
| carbon monoxide [ppm-mol] | 0.5 | 0.01 | nil | nil |
| carbon dioxide [ppm-mol] | 0.8 | 0.1 | 0.2 | 6 |
| sulfur [ppm-wt.] | 3.0 | 0.8 | nil | 1 |
| nitrogen [ppm-mol] | nil | nil | 40 | 100 |
| carbonyl sulfide [ppm-wt.] | 3.5 | 0.01 | nil | nil |
| water [ppm-wt.] | 1.0 | 0.1 | 0.8 | 2 |
| other hydrocarbons (e.g. ethylene) [ppm-mol] | 10 000 | 200 | 200 | 3 500 |

TABLE 2

| | Example 1 | Example 2 | Comparative Example A |
| --- | --- | --- | --- |
| First reactor | | | |
| $H_2/C_2H_4$ molar ratio | 2.6 | 2.6 | 2.5 |
| $C_2H_4$ [vol. %] | 12.3 | 12.3 | 12.3 |
| Density [g/cm³] | 0.969 | 0.969 | 0.965 |
| $MFR_{2.16}$ [g/10 min] | 81 | 79 | 84 |

TABLE 2-continued

|  | Example 1 | Example 2 | Comparative Example A |
|---|---|---|---|
| Second reactor | | | |
| $H_2/C_2H_4$ molar ratio in riser | 0.28 | 0.27 | 0.30 |
| $C_2H_4$ [vol. %] in riser | 12.6 | 12.5 | 12.3 |
| Final polymer properties | | | |
| $MFR_{21.6}$ [g/10 min] | 23.7 | 23.4 | 24 |
| FRR | 19.8 | 19.7 | 20.9 |
| Density [g/cm$^3$] | 0.9579 | 0.9580 | 0.9575 |
| Swell ratio [%] | 173 | 175 | 172 |
| 1-Hexene content [% by weight] | 0.18 | 0.18 | 0.13 |
| FNCT [h] | 18.1 | 18.3 | 12.2 |
| Gel count >700 µm [1/m$^2$] | 0.3 | 0.3 | 1.1 |
| Gel count total [1/m$^2$] | 501 | 480 | 1078 |
| Catalyst productivity [g/g] | 7337 | 7345 | 5780 |

The comparison of Examples 1 and 2 demonstrates that as well purifying a propane stream containing impurities directly before feed to the gas-phase polymerization unit as purchasing high-purity propane allow to produce an ethylene polymer having a good property combination with a high catalyst productivity.

The comparison of Example 2 and Comparative Example A shows that, by using a propane with a higher content of propylene and polar impurities, the environmental stress cracking resistance is reduced, the gel count is increased and the catalyst productivity goes down.

What is claimed is:

1. A process for the preparation of an ethylene polymer, comprising a step of
    forming an ethylene polymer in particle form in a gas-phase polymerization unit comprising a gas-phase polymerization reactor by homopolymerizing ethylene or copolymerizing ethylene and one or more $C_4$-$C_{12}$-1-alkenes at temperatures from 20 to 200° C. and pressures of from 0.5 to 10 MPa in a reaction gas comprising propane as polymerization diluent in the presence of a polymerization catalyst,
    wherein a purified propane feed stream comprising at least 99% mol propane and not more than 100 ppm-mol propylene is fed into the gas-phase polymerization unit and purification of the purified propane feed stream has been carried out by passing a hydrocarbon stream containing propane, propylene, acetylene, carbon monoxide, carbon dioxide, oxygen and water through hydrocarbon purification units which reduce at least a concentration of propylene, acetylene, carbon monoxide, carbon dioxide, oxygen and water contained in the hydrocarbon stream to produce the purified propane feed stream.

2. The process of claim 1, wherein the purified propane feed stream fed to the gas-phase polymerization unit comprises not more than 0.03 ppm-mol carbon monoxide, not more than 0.4 ppm-mol carbon dioxide, not more than 2.0 ppm-mol oxygen, not more than 3.0 ppm-mol acetylene, and not more than 2.0 ppm-mol water.

3. The process of claim 1, wherein activation of a polymerization catalyst is carried out by contacting, in liquid propane as a diluent, a solid catalyst component with an organometallic compound and optionally an electron donor compound to form the polymerization catalyst.

4. The process of claim 3, wherein the liquid propane used as a diluent for the activation of the polymerization catalyst is taken from the purified propane feed stream.

5. The process of claim 1, wherein a hydrocarbon purification unit for preparing the purified propane stream is a catalytic hydrogenation unit.

6. The process of claim 5, wherein the catalytic hydrogenation unit comprises a hydrogenation catalyst which is a platinum-or palladium-based composition on an alumina support.

7. The process of claim 5, wherein a part of the hydrocarbon stream having passed the catalytic hydrogenation unit is recycled to a position upstream of the catalytic hydrogenation unit and mixed with the hydrocarbon stream to be hydrogenated.

8. The process of claim 1, wherein purification of the hydrocarbon stream occurs by subsequently passing the hydrocarbon stream through first a purification unit comprising a Cu based catalyst, then passing a resulting stream through a catalytic hydrogenation unit, thereafter passing a resulting stream through a separation unit and afterward passing a resulting stream through a drying unit.

9. The process of claim 1, wherein the hydrocarbon stream is a purified propylene stream comprising at least 99 mol % propylene.

10. The process of claim 1, wherein the ethylene polymer is a multimodal ethylene polymer and the gas-phase polymerization unit comprises a reactor cascade of two or more gas-phase polymerization reactors which comprises a first polymerization reactor, into which the polymerization catalyst is fed, and one or more subsequent gas-phase polymerization reactors, which receive a polymerization catalyst in active form incorporated into ethylene polymer particles formed in a preceding gas-phase polymerization reactor(s).

11. The process of claim 10, wherein the first gas-phase polymerization reactor of the reactor cascade is a fluidized-bed gas-phase polymerization reactor.

12. The process of claim 11, wherein the fluidized-bed gas-phase polymerization reactor comprises a polymer discharge pipe, which contains a bed of ethylene polymer particles that move from top to bottom of the polymer discharge pipe, and propane is introduced into the polymer discharge pipe in an amount that an upward stream of propane is induced in the bed of ethylene polymer particles above a propane introduction point.

13. The process of claim 10, wherein a subsequent polymerization reactor is a multizone circulating gas-phase polymerization reactor in which a first gas-phase polymerization zone is a riser, wherein growing polyolefin particles flow upward under fast fluidization or transport conditions, and a second polymerization zone is a downcomer, wherein the growing polyolefin particles flow downward in a densified form, wherein the riser and the downcomer are interconnected and polyolefin particles leaving the riser enter the downcomer and polyolefin particles leaving the downcomer enter the riser, thereby establishing a circulation of polyolefin particles through the riser and the downcomer.

14. The process of claim 1, wherein the ethylene polymer is a high density polyethylene having a density determined according to DIN EN ISO 1183-1:2004 at 23° C. from 0.935 g/cm$^3$ to 0.970 g/cm$^3$.

15. A process for the preparation of a multimodal ethylene polymer, comprising the step of
    forming an ethylene polymer in particle form in a gas-phase polymerization unit comprising a reactor cascade of two or more gas-phase polymerization reactors which comprises a first gas-phase polymerization reactor, into which a polymerization catalyst is fed, and one or more subsequent gas-phase polymerization reactors, which receive a polymerization catalyst fed to the first gas-phase polymerization reactor in active form incorporated into ethylene polymer particles formed in a preceding gas-phase polymerization reactor(s) by homopolymerizing ethylene or copolymerizing ethylene and one or more $C_4$-$C_{12}$-1-alkenes at temperatures from 20 to 200° C. and pressures of from 0.5 to 10 MPa in a reaction gas comprising propane as polymerization diluent in the presence of a polymerization catalyst, wherein a purified propane feed stream comprising at least 99% mol propane and not more than 100 ppm-mol propylene is fed into the gas-phase polymerization unit and purification of the purified propane feed stream has been carried out by passing a hydrocarbon stream containing propane, propylene, acetylene, carbon monoxide, carbon dioxide, oxygen and water through hydrocarbon purification units which reduce at least the concentration of propylene, acetylene, carbon monoxide, carbon dioxide, oxygen and water contained in the hydrocarbon stream to produce the purified propane feed stream, and wherein the purified propane feed stream fed to the gas-phase polymerization unit comprises not more than 0.03 ppm-mol carbon monoxide, not more than 0.4 ppm-mol carbon dioxide, not more than 2.0 ppm-mol oxygen, not more than 3.0 ppm-mol acetylene, and not more than 2.0 ppm-mol water.

16. The process of claim 15, wherein activation of the polymerization catalyst is carried out by contacting, in liquid propane as diluent, a solid catalyst component with an organometallic compound and optionally an electron donor compound to form an activated polymerization catalyst and the liquid propane used as a diluent for the activation of the polymerization catalyst is taken from the purified propane feed stream.

17. The process of claim 15, wherein a hydrocarbon purification unit for preparing the purified propane stream is a catalytic hydrogenation unit comprising a hydrogenation catalyst which is a platinum-or palladium-based composition on an alumina support.

18. The process of claim 17, wherein a part of the hydrocarbon stream having passed the catalytic hydrogenation unit is recycled to a position upstream of the catalytic hydrogenation unit and mixed with the hydrocarbon stream to be hydrogenated.

19. The process of claim 15, wherein purification of the hydrocarbon stream occurs by subsequently passing a hydrocarbon stream through first a purification unit comprising a Cu based catalyst, then passing a resulting stream through a catalytic hydrogenation unit, thereafter passing a resulting stream through a separation unit and afterwards passing a resulting stream through a drying unit.

20. The process of claim 15, wherein the hydrocarbon stream for preparing the purified propane feed stream is a purified propylene stream comprising at least 99 mol % propylene.

* * * * *